(12) United States Patent
Engl et al.

(10) Patent No.: US 8,291,766 B2
(45) Date of Patent: Oct. 23, 2012

(54) METHOD AND DEVICE FOR ULTRASOUND TESTING

(75) Inventors: Günter Engl, Erlangen (DE); Friedrich Mohr, Nürnberg (DE); Michael Kröning, Saarbrücken (DE); Krishna Mohan Reddy, Chennai (IN)

(73) Assignee: Intelligendt Systems & Services GmbH, Erlangen (DE)

( * ) Notice: Subject to any disclaimer, the term of this patent is extended or adjusted under 35 U.S.C. 154(b) by 298 days.

(21) Appl. No.: 12/781,055

(22) Filed: May 17, 2010

(65) Prior Publication Data

US 2010/0307252 A1 Dec. 9, 2010

(30) Foreign Application Priority Data

May 15, 2009 (DE) .......................... 10 2009 021 586
Nov. 30, 2009 (DE) .......................... 10 2009 047 318

(51) Int. Cl.
*G01N 29/34* (2006.01)
(52) U.S. Cl. ............................................ 73/632; 73/602
(58) Field of Classification Search .................... 73/632, 73/599, 602, 618, 619, 620, 622, 627, 628, 73/633; 702/39, 104
See application file for complete search history.

(56) References Cited

U.S. PATENT DOCUMENTS

| | | | | |
|---|---|---|---|---|
| 4,102,205 A | * | 7/1978 | Pies et al. | 73/626 |
| 4,134,081 A | * | 1/1979 | Pittaro | 331/1 A |
| 4,362,566 A | | 12/1982 | Hinterwaldner | |
| 4,492,118 A | * | 1/1985 | Bathmann et al. | 73/612 |
| 4,640,132 A | | 2/1987 | Flora et al. | |
| 4,805,459 A | * | 2/1989 | Ferreira | 73/620 |
| 5,143,072 A | * | 9/1992 | Kantorovich et al. | 600/437 |
| 5,628,319 A | * | 5/1997 | Koch et al. | 600/437 |
| 5,675,085 A | * | 10/1997 | Hayashi et al. | 73/628 |
| 5,963,882 A | * | 10/1999 | Viertl et al. | 702/39 |
| 6,541,134 B1 | * | 4/2003 | Strangman et al. | 428/698 |

FOREIGN PATENT DOCUMENTS

| | | |
|---|---|---|
| DE | 2701054 A1 | 7/1978 |
| EP | 2051070 A1 | 4/2009 |
| JP | 9292374 A | 11/1997 |

OTHER PUBLICATIONS

Pignone, E, Enhancement in Image Quality in Ultrasonic Flaw Detection Process in Rotor Turbine Using SAFT, IEEE 1st 2004—International Workshop on Imaging Systems and Techniques, Stresa, Italy, May 14, 2004, pp. 117-122.

* cited by examiner

*Primary Examiner* — J M Saint Surin
(74) *Attorney, Agent, or Firm* — Laurence A. Greenberg; Werner H. Stemer; Ralph E. Locher

(57) ABSTRACT

In a method and device for ultrasonic testing of a workpiece, a multiplicity of ultrasonic testing pulses are launched into the workpiece from a test surface thereof. At least two ultrasonic testing pulses are launched into the workpiece to be tested at launching points that are spaced apart from one another by a test step width measured along the test surface. A single measured value (T) assigned to a local point located in the workpiece is calculated on the basis of the received signals assigned to the at least two ultrasonic testing pulses.

15 Claims, 3 Drawing Sheets

METHOD AND DEVICE FOR ULTRASOUND TESTING

Figure 1:
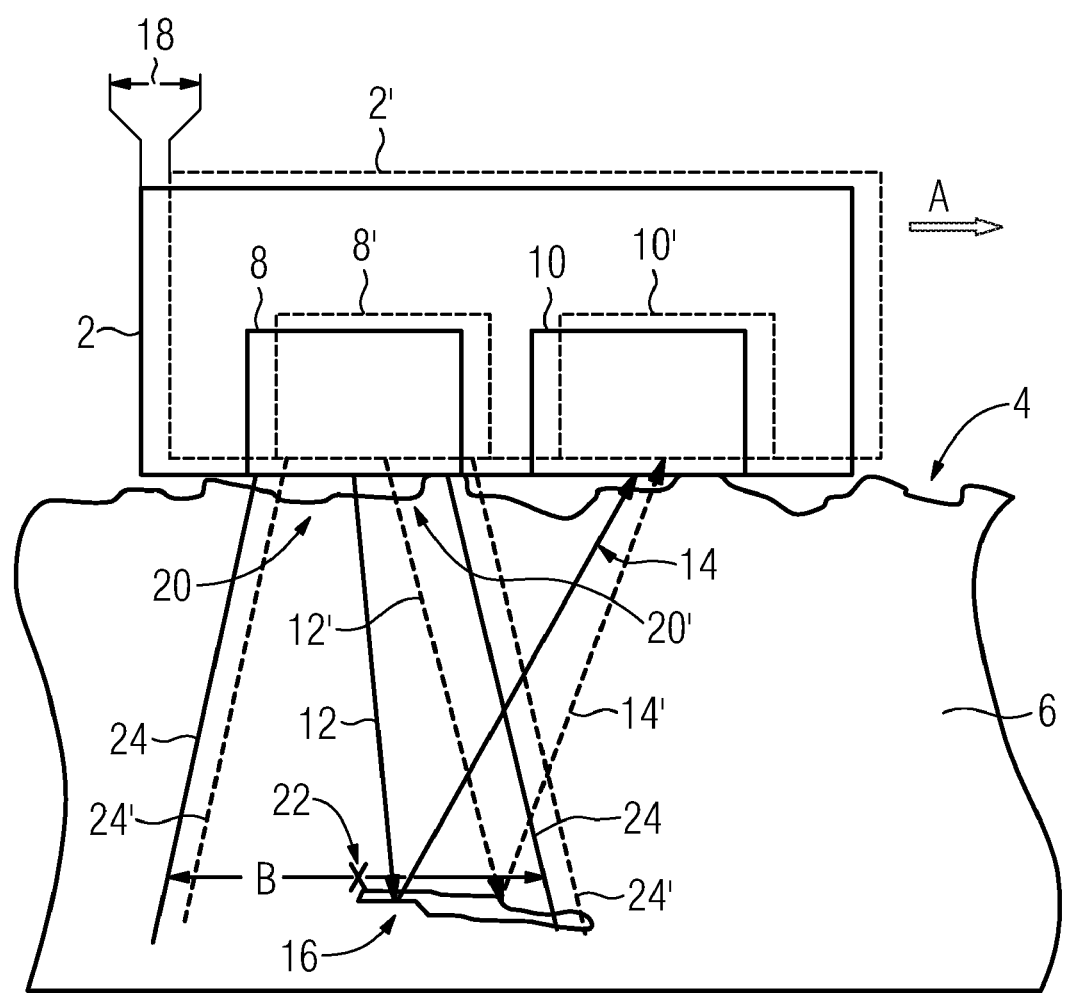

It is possible to use ultrasound to detect flaws and/or imperfections in the volume and on the surfaces of components, including technical ones. One advantage of the pulse-echo technique preferably used in ultrasonic testing is the excellent detectability of planar separations such as, for example, cracks. Ultrasonic tests are used both in fabrication as integrated testing for the purpose of quality assurance, and as recurring testing in the context of servicing and maintenance for the purpose of ensuring further fitness for use of the test object.

In order to carry out an ultrasonic test, an ultrasound head is put on a test surface of a workpiece to be tested by using a suitable coupling medium. However, special requirements are placed on the nature of such a test surface in order to ensure a uniform testing sensitivity and reproducibility of the test results. As a rule, the framework of rules set up for the ultrasonic testing therefore restricts the surface qualities in such a way that its roughness and/or waviness must lie within certain prescribed limits. In particular, the surface roughness and/or waviness is not allowed to lead to gaps between test head and test surface that are greater than half the wavelength of the nominal frequency used for testing. If these conditions are not met, the sound field used for testing and launched into the relevant workpiece is greatly impaired in amplitude and phase. Testing conforming to the framework of rules is substantially compromised if not, indeed, impossible in such a case. Thus, in summary ultrasonic testing has been restricted to date to well-defined surface qualities.

In order to satisfy the requirements of the framework of rules, the test surfaces are prepared properly for testing. This takes place, for example, by slightly grinding the surface so that the roughness thereof is subsequently below a certain limit value.

If it is impossible or excessively uneconomic for the test surface to be prepared in such a way, the test specifications may be adapted within certain limits to the surface conditions. This takes place, for example, by selection of low testing frequencies, although to the extent that the required testing sensitivity can be satisfied. However, in the end a change to the framework of testing rules is always a compromise between robust conduct of testing and good flaw detection capability.

Similar problems arise for workpieces with acoustically anisotropic coatings, for example in the case of welded austenitic platings such as are usual in pressure vessel construction. Here, as well, the coating influences the passage of sound such that the framework of rules must equally be adapted as in the case of rough or wavy test surfaces. However, as already mentioned, this is possible only within certain limits. Furthermore, the passage of sound through the coating can be stabilized within certain limits by optimizing the sound field parameters, for example the focusing, type of focusing, pulse duration or a suitable mode selection. However, it is necessary as a rule to furnish appropriate test certificates for the respective form of the workpiece.

In some cases, however, it will generally be required to retest with complementary techniques, for example by eddy-current testing, in addition to the ultrasonic testing. This applies in particular whenever the obstacles to testing are present merely in a spatially limited fashion. However, additional test measures lead to increased test costs prompted by the fact that the informativeness of the testing, while still remaining adequate, is nevertheless worse, as a rule.

It is an object of the present invention to specify a method and a device for ultrasonic testing, which method or device is an improvement over the prior art.

The object is achieved according to the invention by a method as claimed in claim 1, and by a device as claimed in claim 13. Advantageous refinements are the subject matter of the dependent claims.

In the inventive method, a multiplicity of ultrasonic testing pulses are launched into a workpiece from a test surface thereof. At least two of this multiplicity of ultrasonic testing pulses are launched into the workpiece to be tested at launching points spaced apart from one another. In this case, the corresponding launching points are separated by a test step width measured along the test surface. A single local point located in the workpiece is now assigned a single measured value that is based on those received signals that are assigned to the at least two ultrasonic testing pulses. In other words, a local point is assigned a measured value that is calculated from at least two received signals. Said received signals result from reflection in the workpiece and are assigned to the corresponding at least two ultrasonic testing pulses launched into the workpiece.

The inventive method is based on the following findings:

During the ultrasonic testing of a workpiece with a rough surface, starting from which the ultrasonic testing pulses used to test the workpiece are coupled into the workpiece, also referred to as test surface, the roughness of the test surface influences both the launching and the decoupling of the corresponding ultrasonic fields.

A rough surface is always understood as such a surface of a workpiece to be tested that has not been subjected to the customary pretreatments, such as grinding, polishing etc, for example, that are typically carried out in advance of ultrasonic testing. By way of example, a forged workpiece or semi-finished product has such a rough surface.

It has been found that the influence of the roughness of the test surface on the result of the ultrasonic testing differs slightly at each point of the test surface. In order to minimize the influence of the surface roughness on the result of the ultrasonic testing, one or more ultrasonic testing pulses are launched into the workpiece to be tested at mutually differing launching points of the test surface. The separation between the launching points is, however, now selected to be so slight that without the disturbing influence of the rough surface the measured data attained would supply virtually identical information relating to the reflectors present in the volume of the test body or workpiece.

Depending on the position of the launching point on the test surface, the measured measurement or echo signal is subject to slightly different disturbing influences that are defined by the roughness of the test surface. The actual information content of the associated echo signals that is defined by the position of the reflectors in the volume of the workpiece changes only extremely little, however. This difference in the information content can be neglected.

The variations defined by the roughness of the test surface come about because as it changes position on the test surface the ultrasonic test head always encounters slightly modified local conditions. More precisely, the interface present between the ultrasonic test head or a coupling medium used and the rough test surface varies slightly. Because of this local variation, the conditions under which an ultrasonic testing pulse is launched and the echo signal is decoupled will always differ slightly from one launching point to the next.

It has, however, been found that the roughness of the test surface influences the result of the ultrasonic testing stochastically. A plurality of echo signals are combined in order to minimize this stochastic influence of the surface roughness. It is essential in this context that the relevant echo signals or measured values come from those ultrasonic testing pulses that have been injected into the workpiece to be tested at mutually differing launching points. The individual launching points are now situated so close to one another that although the local launching conditions vary from one launching point to the next, the received measurement signals can nevertheless be assigned to one and the same local point of the workpiece to be tested.

Data that are redundant per se but are subject to a scatter defined by the surface roughness are obtained in this way. Since the influence of the surface roughness is stochastic, the result of the ultrasonic testing can largely be freed from the disturbing influence of the surface roughness with the aid of statistical methods, in the simplest case by averaging.

It is thereby advantageously possible to dispense with a time-consuming and cost-intensive pretreatment of the test surface without the informativeness and quality of the ultrasonic measurement suffering thereby in a counter move. Consequently, the inventive method is suitable, in particular, for testing workpieces with a rough, untreated test surface, and/or it permits for the first time the ultrasonic testing of such untreated workpieces.

However, the inventive method is now based on the finding that modern ultrasonic technology has means available which permit an exact detection of the position of the ultrasonic test head, and processing of the large data volumes produced, ideally in real time. These techniques are now advantageously used to debug ultrasonic data.

Ultrasonic technology can therefore advantageously advance into a novel field of application. For example, it is now possible to test forged semifinished products given an untreated and therefore rough surface. This is accompanied by substantial advantages in the production of such components, since flaws can be detected very early. Further processing operations can be adapted, or be omitted, and this substantially simplifies production planning. Again, in the case of weld-clad components that impair the passage of sound, it is possible to improve ultrasonic testing in the direction of testing conforming to the framework of rules. However, the inventive method provides the preconditions for the application of tomographic techniques.

In accordance with a first embodiment, the ultrasonic testing is performed with the aid of an ultrasonic test head placed on the test surface. The test step width is selected in this case to be smaller than a lateral position resolution that is prescribed by the design of the ultrasonic test head and by the operating parameters thereof during the ultrasonic testing. The design of the ultrasonic test head can influence the lateral resolution, for example by the lateral dimensions of the ultrasonic transducer used, for example a piezoelement. If a transducer array is used as ultrasonic transmitter, the size thereof, that is to say the dimensions of the entire array and the spacing of the individual transducer elements from one another, determines the resolution of the ultrasonic test head. Operating parameters that influence the lateral resolution are, for example, the nominal frequency of the ultrasonic pulses used for testing or, in the case of a transducer array, the focusing set by phase-delayed driving of the transducer elements.

Since, as previously, the individual ultrasonic testing pulses are launched into the workpiece to be tested at launching points of the test surface that are spaced apart from one another, the influence of the surface roughness on the received echo signals varies. However, the test step width is now selected to be so small that it lies below an achievable lateral resolution. Consequently, it is advantageously possible to use a plurality of echo signals in order to determine an individual measured value that is assigned to a single local point located in the workpiece, without the lateral local resolution of the ultrasonic method decreasing.

In accordance with a further embodiment, the calculation of the measured value is preceded by a statistical evaluation of the received signals. In the case of the subsequent calculation of the measured value, no account is taken of those received signals that exceed a limit value determined in the course of the prior statistical evaluation. This limit value is preferably a multiple of, furthermore preferably twice, a statistical standard deviation of the evaluated received signals. The received signals influenced by the roughness of the test surface can have the noise removed by statistical analysis and subsequent selection. This takes place by taking no account of statistical outliers that lie outside a breadth of scatter determined with the aid of the remaining values. A precise result of low noise is attained thereby. Since both the amplitude and the phase of the received signals are influenced as a rule, both the amplitude and the phase are taken into account in debugging.

The statistical evaluation can be simple methods known per se if the latter are sufficient. In the case of complex statistics of the interference caused by the rough surface, it is additionally possible to make appropriate use of suitable methods, for example based on maximum entropy algorithms that are preferably capable of real-time programming. The selection of the statistical method is made with reference to the problem.

Furthermore, it is possible to monitor the measured statistics of the disturbing influences caused by the roughness of the test surface or an acoustically anisotropic coating, since said statistics include further information of interest for testing purposes. In addition to making statements about the test surface and/or the coating itself, such an evaluation can be used to assess the carrying out of the test. Thus, for example, such an evaluation supplies data that permit an assessment of the coupling of the test head to the workpiece to be tested.

In accordance with a further embodiment, an ultrasonic test head provided for the ultrasonic testing is moved along a scan path at least in a time interval between the launching of the at least two ultrasonic testing pulses. In this case, the ultrasonic fields of consecutive ultrasonic testing pulses that are launched into the workpiece to be tested preferably overlap. It is preferred for this overlap to be at least 10%, and furthermore for it to be 90%.

A certain overlap of the sound field regions of the ultrasonic testing pulses with an adequate flaw detection sensitivity is always required for complete coverage of a test volume. This holds, in particular, for the calculation of the track offset, for example in the case of meandering scanning of the test surface. More or fewer redundant data records are produced during ultrasonic testing by now selecting this overlap to be more or less pronounced or large. This "oversampling" serves the purpose of improving the statistical evaluation of the measured values. Since a plurality of received signals are always assigned to a single local point of the workpiece to be tested, the statistics that can be achieved are better the greater the number of data records, that are based on testing pulses launched at different launching points, that can be used as a basis for the calculation. Since methods for efficient real-time signal processing are available to modern ultrasonic technology, such "oversampling" can be implemented in conjunction with acceptable system costs.

In accordance with a further embodiment, the measured value is calculated on the basis of those received signals that follow one another in the scan direction. A prescribed number of received signals are preferably combined to form a data block, it being further preferred for the respectively current received signal and a prescribed number of preceding received signals to be combined to form a data block. In accordance with a development, the number of those received signals that are combined to form a data block can be varied as a function of the position of the ultrasonic test head on the scan path. It can be advantageous for some applications for the number of the measured values which "move along with" the test head not to be kept constant.

The remarks made in conjunction with the method are valid by analogy with regard to their effects and advantages for the inventive device.

Figure 2:
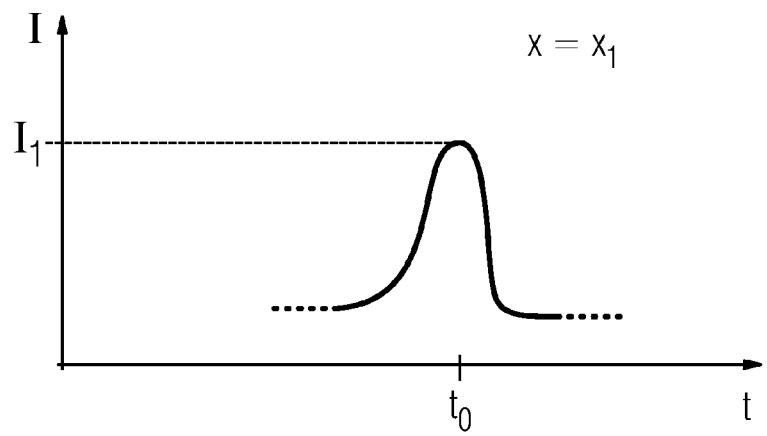
Figure 3:
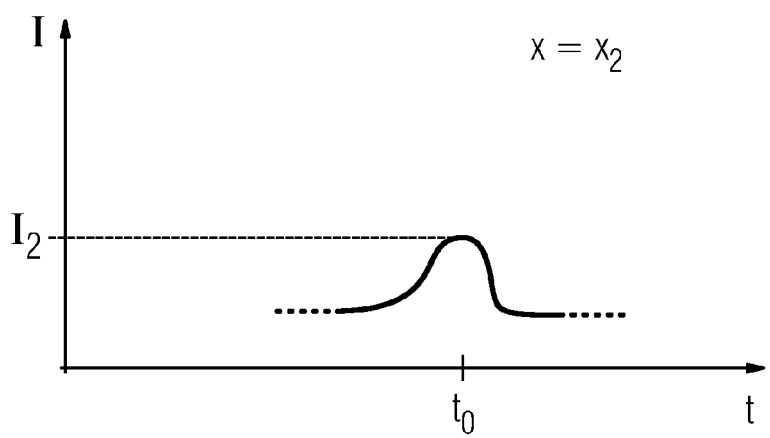
Figure 4:
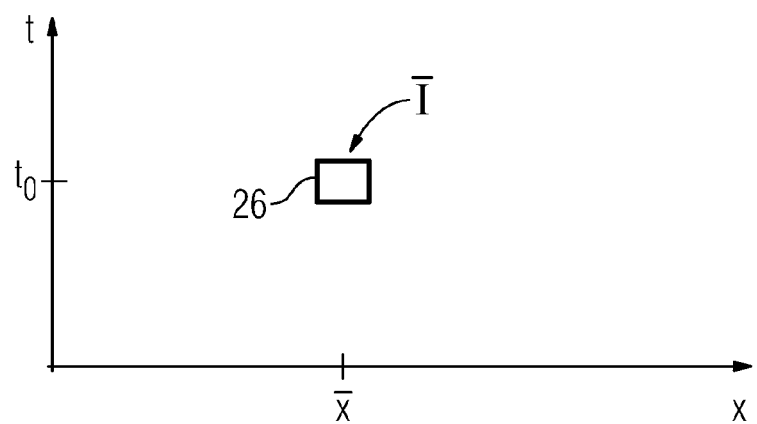
Figure 5A:
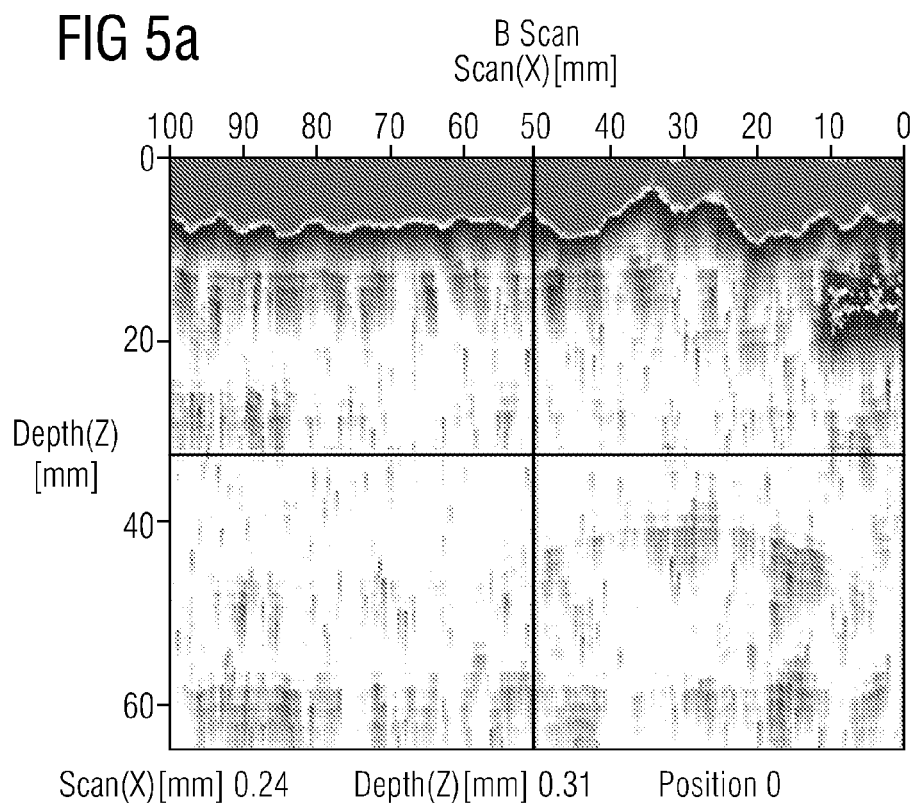

The invention is explained in more detail below with reference to the figures of the drawing, in which:

FIG. 1 shows an ultrasonic test head placed on a workpiece,

FIGS. 2 and 3 respectively show an A image at mutually differing local positions, FIG. 4 shows a schematic B image calculated from the A images of FIGS. 2 and 3, FIGS. 5a and b respectively show a B image recorded under real conditions.

FIG. 1 shows a testing situation in which an ultrasonic test head 2 is placed on a rough test surface 4 of a workpiece 6. The testing situation is illustrated in a very shortened fashion in a direction perpendicular to the test surface 4 for reasons of clarity. To be accurate, two testing situations are illustrated in FIG. 1. The ultrasonic test head 2 illustrated with the solid line shows a first testing situation, while a further ultrasonic test head 2' illustrated with a dashed line shows a second testing situation. Reference numerals relating to the first testing situation are provided in unprimed fashion, while reference numerals relating to the second testing situation are provided in primed fashion. A coupling medium generally used is not illustrated in FIG. 1, for reasons of clarity.

The aim is firstly to go into the first testing situation in more detail. The ultrasonic test head 2 comprises a transmitting element 8 and a receiving element 10, with the aid of which elements an ultrasonic testing pulse 12 is launched into the workpiece 6, the echo or received signal 14 of which is received. When the ultrasonic testing pulse 12 is launched into the workpiece 6, it passes the rough test surface 4, that is to say the interface between the coupling medium (not illustrated in FIG. 1) and the workpiece 6. The roughness of the test surface 4 influences the amplitude and phase of the ultrasonic testing pulse 12 launched into the workpiece 6. The same holds when the received signal 14 reflected at a flaw 16 present in the workpiece 6 leaves the workpiece 6 and re-passes the rough test surface 4, this time in the direction of the receiving element 10. After one or more ultrasonic testing pulses 12 have been launched into the workpiece 6, the ultrasonic test head 2 is brought from the first position into the second position. This takes place by virtue of the fact that the ultrasonic test head 2 is displaced by one test step width 18 in the direction of a scan path A.

In the second testing situation, one or more ultrasonic testing pulses 12' are once again launched into the workpiece 6 and corresponding received signals 14' are received. The workpiece 6 can be tested along the scan path A by subsequent renewed displacement.

The workpiece 6 can, for example, be a raw-forged steel block, a shaft, etc, that is tested along its circumference or length from the outside or inside. The example shown in FIG. 1 is not restricted to a workpiece 6 with raw test surface 4. The method described below can equally be applied in the case of workpieces 6 with an acoustically anisotropic coating, which is located in the region of the test surface 6, and to workpieces with a coarse-grained structure.

In the first position of the ultrasonic test head 2 (provided with unprimed reference numerals), the ultrasonic testing pulse 12 is launched into the workpiece 6 at a first launching point 20. In the second position (provided with primed reference numerals), the ultrasonic testing pulse 12' is launched into the workpiece 6 at a second launching point 20'. The two launching points 20, 20' delimit the test step width 18 measured in the direction of the test surface 4 of the workpiece.

Since the test step width 18 between the first and second positions of the ultrasonic test head 2, 2' shown in FIG. 1 is selected to be so slight that it is less than a lateral resolution (that is to say one in the direction of the extent of the test surface 4) of the ultrasonic test head 2, 2' that can be reached in the test arrangement shown, the received signals 14, 14' received respectively in the first and second positions of the ultrasonic test head 2, 2' can be assigned to a common local point 22 inside the workpiece 6. The lateral local resolution of the measurement is determined by the width B of the ultrasonic field in the depth of the reflecting flaw 16, which field is launched into the workpiece 6. The ultrasonic field is illustrated in FIG. 1 with the aid of its limiting rays 24, 24'. In other words: reflectors present in the workpiece such as, for example, the flaw 16 which can lie within the ultrasonic field of a testing pulse 12, 12' cannot be detected separately from one another in a lateral direction. For this reason, a point in the middle of the ultrasonic field is taken as local point 22. The local point 22 shown in FIG. 1 is the first local point assigned to the first position of the ultrasonic head 2.

The received signal 14 received by the receiving element 10 at the first position of the ultrasonic test head 2, which is to be denoted below by $x_1$, is illustrated as A image in FIG. 2. The intensity I is plotted against the time t, which corresponds to the depth, in FIG. 2. The reflection found at the instant $t_0$, which is intended to correspond to the depth of the flaw 16 in the workpiece 6, has an intensity $I_1$. After the ultrasonic test head 2' has been displaced into its second position, which is to be denoted below by $x_2$, the received signal 14' has the intensity $I_2$. The corresponding A image is illustrated in FIG. 3.

In an associated B image that is shown in FIG. 4, the intensity I of the reflections found in the received signals 14, 14' is illustrated in a fashion coded for color and intensity. The corresponding propagation time t or depth is illustrated for various positions x in this case. Illustrated by way of example in FIG. 4 is a pixel 26 whose intensity in terms of color and grey scale value (not illustrated for reasons of clarity) corresponds to the intensity $\bar{I}$ of the reflection found at the position $\bar{x}$ at the depth $t_0$. In the example illustrated, this reflection originates from the flaw 16 present in the workpiece. Since the pixel 26 is calculated on the basis of a plurality of received signals 14, 14' and its result is allocated to a mean location, the local position $\bar{x}=(x1+x2)/2$ and the intensity $\bar{I}=(I1+I2)/2$ are valid for the instant $t_0$, for example. Since the received signals on which this measured value is based are based on ultrasonic testing pulses 12, 12' which were launched into the workpiece 6 at launching points 20, 20' differing only slightly from one another in the scan direction A, the influence of the roughness of the test surface on each of the received signals 14, 14' is slightly different. A mean intensity $\bar{I}$ relating to a mean spatial coordinate $\bar{x}$ is calculated by the averaging undertaken over the spatial coordinate x. This averaging can substantially reduce the influence of the surface roughness on the measurement result attained. In other words, the measured value $\bar{I}$ is assigned to a local point 22 determined by the coordinates $\bar{x}$ and $t_0$. In FIG. 1, this local point would lie between the illustrated local point 22, located in the middle between the limiting rays 24 of the ultrasonic field of the first testing pulse 12 at the depth of the flaw 16, and a further local point constructed in an analogous way for the second position of the ultrasonic test head 2'.

The averaging, previously explained by way of example of two intensities I1 and I2 is merely the simplest possibility of noise suppression. Further improvement is served by so-called "entropy algorithms", which are based on the principle that the entropy of the amount of the measured information is maximized. This can be formulated in a very different way, for example through specific assumptions relating to the discretization of the local information.

Figure 5B:
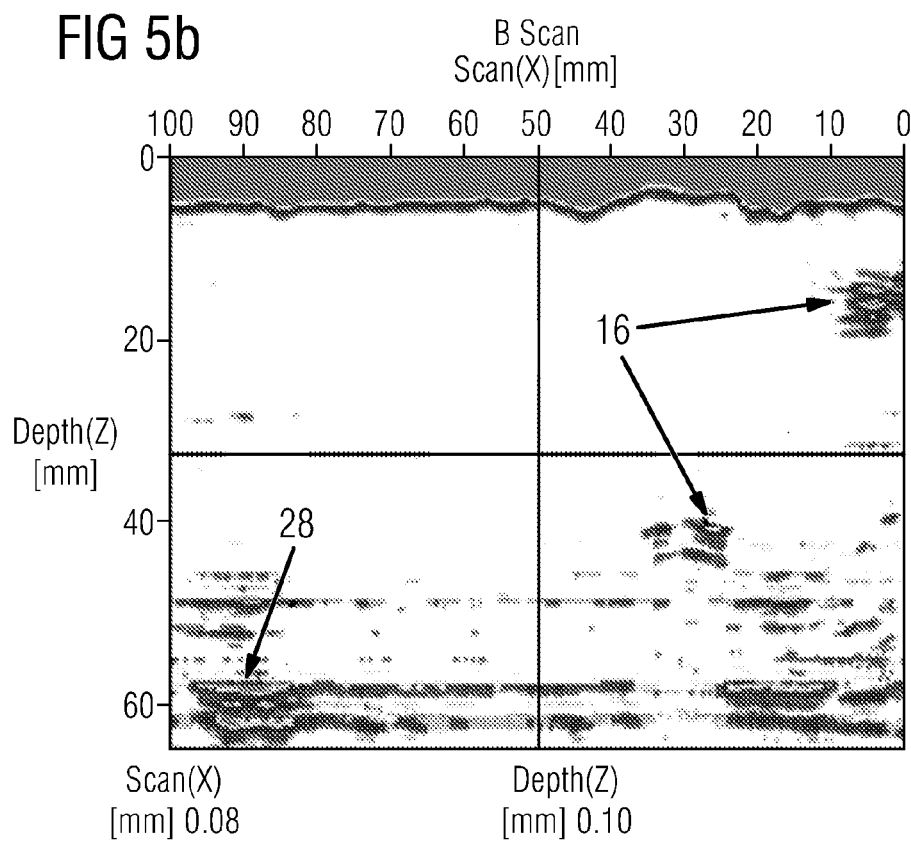

FIGS. 5a and b show the result of an ultrasonic test carried out under real conditions on a test body. FIG. 5a shows here the result of a conventional measurement. Illustrated in FIG. 5b is the result of a measurement carried out under the same conditions but for which the inventive method was used. FIG. 5b conspicuously shows the image with substantially less noise. This is clear, in particular, from the substantially lower noise, in comparison to FIG. 5a, caused by the surface roughness, at the upper image edge. Moreover, because of the fact that FIG. 5a concerns a coarse-grained test body it shows a high level of noise and severe attenuation in the volume. Because of this, there is no back wall signal in FIG. 5a. A back wall signal 28 is to be found in FIG. 5b by using the inventive method. The effect of the inventive method is rendered more evident by the flaw 16 present in the measurements illustrated. Whereas it is still possible to detect the flaws 16 present in the upper region of FIGS. 5a and b in the conventional measurement as well (compare FIG. 5a), the deeper-lying flaw 16 in the lower part of FIG. 5b can be reliably found only with the aid of the inventive method.

The invention claimed is:

1. A method for ultrasonic testing of a workpiece, the method which comprises:
    launching a multiplicity of ultrasonic testing pulses into the workpiece from a test surface thereof, and thereby launching at least two of the ultrasonic testing pulses into the workpiece to be tested at launching points spaced apart from one another by a given test step width measured along the test surface;
    placing an ultrasonic test head on the test surface and generating the testing pulses with the test head, and selecting the test step width to be smaller than a lateral position resolution prescribed by a design of the ultrasonic test head and operating parameters thereof during the ultrasonic testing process;
    receiving signals representing measured values from the workpiece in response to the at least two ultrasonic testing pulses; and
    calculating a single measured value (I) assigned to a local point in the workpiece on a basis of the received signals associated with and received in response to the at least two ultrasonic testing pulses.

2. The method for ultrasonic testing according to claim 1, which comprises providing an ultrasonic test head and moving the ultrasonic test head along a scan path during a time interval between a launch of the at least two ultrasonic testing pulses.

3. The method for ultrasonic testing according to claim 2, wherein ultrasonic fields of the at least two consecutive ultrasonic testing pulses launched into the workpiece overlap one another.

4. The method for ultrasonic testing according to claim 3, wherein the ultrasonic fields overlap one another by at least 10%.

5. The method for ultrasonic testing according to claim 2, which comprises calculating the measured value (I) on a basis of those received signals that follow one another in the scan direction.

6. The method for ultrasonic testing according to claim 5, which comprises combining a prescribed number of received signals to form a data block.

7. The method for ultrasonic testing according to claim 5, which comprises combining a respectively current received signal and a prescribed number of preceding received signals to form a data block.

8. The method for ultrasonic testing according to claim 7, which comprises varying the prescribed number of the received signals as a function of a position of the ultrasonic test head on the scan path.

9. A device for the ultrasonic testing of a workpiece, the device comprising:
    an ultrasonic head configured to emit ultrasonic pulses into the workpiece and to receive signals from the workpiece; and
    a control and evaluation unit connected to said ultrasonic head and configured to carrying out the method according to claim 1.

10. A method for ultrasonic testing of a workpiece, the method which comprises:
    launching a multiplicity of ultrasonic testing pulses into the workpiece from a test surface thereof, and thereby launching at least two of the ultrasonic testing pulses into the workpiece to be tested at launching points spaced apart from one another by a given test step width measured along the test surface;
    receiving signals representing measured values from the workpiece in response to the at least two ultrasonic testing pulses;
    calculating a single measured value (I) assigned to a local point in the workpiece on a basis of the received signals associated with and received in response to the at least two ultrasonic testing pulses; and
    prior to the step of calculating the measured value (I), carrying out a statistical evaluation of the received signals, and in the case of the calculation of the measured value (I), not taking into account those received signals that exceed a limit value determined in the course of the statistical evaluation.

11. The method for ultrasonic testing according to claim 10, which comprises setting the limit value to a multiple of a statistical standard deviation.

12. A device for the ultrasonic testing of a workpiece, the device comprising:
    an ultrasonic head configured to emit ultrasonic pulses into the workpiece and to receive signals from the workpiece; and
    a control and evaluation unit connected to said ultrasonic head and configured to carrying out the method according to claim 10.

13. A method for ultrasonic testing of a workpiece, the method which comprises:
    launching a multiplicity of ultrasonic testing pulses into the workpiece from a test surface thereof, and thereby launching at least two of the ultrasonic testing pulses into the workpiece to be tested at launching points spaced apart from one another by a given test step width measured along the test surface;
    receiving signals representing measured values from the workpiece in response to the at least two ultrasonic testing pulses;

calculating a single measured value (Ī) assigned to a local point in the workpiece on a basis of the received signals associated with and received in response to the at least two ultrasonic testing pulses; and carrying out a statistical evaluation of the received signals by way of a maximum entropy algorithm.

14. The method for ultrasonic testing according to claim 13, which comprises carrying out the statistical evaluation prior to the step of calculating the measured value (Ī) and not taking into account those received signals that exceed a limit value determined in the course of the statistical evaluation.

15. A device for the ultrasonic testing of a workpiece, the device comprising:
- an ultrasonic head configured to emit ultrasonic pulses into the workpiece and to receive signals from the workpiece; and
- a control and evaluation unit connected to said ultrasonic head and configured to carrying out the method according to claim 13.

* * * * *